US005840945A

United States Patent [19]

Tsujiwaki et al.

[11] Patent Number: 5,840,945

[45] Date of Patent: Nov. 24, 1998

[54] METHOD FOR REFINING AND MANUFACTURING FATS AND OILS CONTAINING POLYUNSATURATED FATTY ACIDS

[75] Inventors: Yoshikazu Tsujiwaki; Hiroshi Yamamoto; Kazuko Hirata, all of Kobe; Satoru Kamigasa, Kurayoshi, all of Japan

[73] Assignee: Ueda Oils and Fats Mfg. Co., Ltd., Kobe, Japan

[21] Appl. No.: 741,683

[22] Filed: Oct. 31, 1996

[30] Foreign Application Priority Data

Nov. 13, 1995 [JP] Japan .................................... 7-294504

[51] Int. Cl.[6] .................................................... C07C 51/43

[52] U.S. Cl. .......................... 554/192; 554/175; 554/191; 554/193; 554/196

[58] Field of Search .................................... 554/191, 196, 554/192, 175, 193

[56] References Cited

U.S. PATENT DOCUMENTS 5,252,762 10/1993 Denton .................................... 554/196
5,466,441 11/1995 Fisher et al. .............................. 424/61

FOREIGN PATENT DOCUMENTS 0324093 7/1989 European Pat. Off. .
0507217 10/1992 European Pat. Off. .

OTHER PUBLICATIONS

Database WPI, Section Ch, Week 9517, Derwent Publications Ltd., London, GB; Class D13, AN 95–125653, XP002038776 & JP 07 047 266 A (Showa Kagaku Kogyo KK), Feb. 21, 1995, abstract.

Database WPI, Section Ch, Week 7750, Derwent Publications Ltd., London, GB; Class D23, AN 77–89262Y, XP002038777 & JP 52 132 007 A (Hara K), Nov. 5, 1977, abstract.

*Primary Examiner*—Gary Geist
*Assistant Examiner*—Deborah D. Carr
*Attorney, Agent, or Firm*—Wenderoth, Lind & Ponack, L.L.P.

[57] ABSTRACT

A method of refining and manufacturing a fat and oil containing polyunsaturated fatty acids which prevents production of peculiar fishy smells when such a fat and oil is added to food materials and while it is stored by preventing oxidation of PUFA's and restraining conversion of odor-emanating precursors into odor-emanating substances. A fat and oil, such as a marine animal oil, containing polyunsaturated fatty acids with 18 or more carbon atoms and three or more double bonds such as EPA and DHA is alkali refined and bleached. The thus alkali refined and bleached fat and oil is refined by bringing 100 parts by weight of it into contact for 10 minutes or more at 5°–80° C. with not less than 0.1 part by weight of powdered or granulated diatomaceous earth formed by calcining with a flux added such as sodium carbonate or sodium chloride. The fat and oil thus obtained is filtered and deodorized by steam distillation under vacuum.

3 Claims, No Drawings

METHOD FOR REFINING AND MANUFACTURING FATS AND OILS CONTAINING POLYUNSATURATED FATTY ACIDS

BACKGROUND OF THE INVENTION

This invention relates to a method for refining and manufacturing fats and oils containing polyunsaturated fatty acids and used as foods, drugs and cosmetics.

Docosahexaenoic acid (hereinafter abbreviated to DHA), eicosapentaenoic acid (abbreviated to EPA) and α-linolenic acid are polyunsaturated fatty acids (abbreviated to PUFA) having 18 or more carbon atoms and three or more double bonds. Such PUFA's lower cholesterol and neutral fat levels in the blood, and suppress aggregation of platelets. Among such PUFA's, DHA, which is present especially in rich amounts in the brain, retinas, testicles and human milk, is believed to be a substance essential for the development of the nervous system.

Therefore, efforts have been made to develop foods and medicines that contain marine animal fats and oils, especially fish oils, which contain PUFA in large amounts.

But PUFA-containing fats and oils have peculiar unpleasant smells. For example, fish oils have fishy smells. Thus, such oils are not used so widely in food materials.

Fish oils obtained from tunas and skipjack, which contain DHA in high concentrations, can be made tasteless and odorless by refining and deodorization. But while the thus refined and deodorized fish oils are stored, the PUFA's double bonds are oxidized by oxygen in the air. Mainly due to this, the oils begin to emanate peculiar fishy smells again.

In order to suppress PUFA's oxidation, antioxidants such as tocopherols, ascorbic acid or lecithin are often added. But it is still difficult to prevent the recurrence of fishy and other unpleasant smells.

In order to hide such recurring smells, odor suppressors and masking agents were used. But it was still impossible to sufficiently suppress odors. Also, the effects of such agents are short-lived, so that they cannot offer a fundamental solution to the odor problem.

From the fact that the addition of antioxidants cannot prevent perfectly the recurrence of odors, the inventors of the present invention, thought that factors other than oxidation may be playing a role in the recurrence of odors. More specifically, they thought that trace amounts of precursors of the odor-emanating substances that remain unremoved by the conventional refining method might convert into odor-emanating substances which, in cooperation with the odors due to oxidation of the double bonds in PUFA's, produce peculiar fishy odors, lowering the market value of the oil products.

Similarly, PUFA containing vegetable oils such as perilla oil and linseed oil also produce unpleasant odors in the same mechanism as with fish oils.

An object of this invention is to provide an improved method of refining and manufacturing a fat and oil containing polyunsaturated fatty acids which prevents production of peculiar fishy smells when such a fat and oil is added to food materials and while it is stored by preventing oxidation of PUFA's and restraining conversion of odor-emanating precursors into odor-emanating substances.

SUMMARY OF THE INVENTION

According to this invention, there is provided a method of refining an oil containing polyunsaturated fatty acids having 18 or more carbon atoms and three or more double bonds, the method comprising the step of bringing 100 parts by weight of the oil into contact for 10 minutes or more at 5°–80° C. with not less than 0.1 part by weight of powdered diatomaceous earth formed by calcining with a flux added.

There is also provided a method of manufacturing an oil containing polyunsaturated fatty acids, the method comprising the steps of alkali refining and bleaching an oil containing polyunsaturated fatty acids having 18 or more carbon atoms and three or more double bonds, bringing 100 parts by weight of the oil into contact with 0.1 part by weight of powdered diatomaceous earth formed by calcining with a flux added for 10 minutes or more at 5°–80° C., filtering the oil, and deodorizing the oil by steam distillation under vacuum.

The PUFA-containing oil used in this invention may be any oil containing polyunsaturated fatty acids having 18 or more carbon atoms and three or more double bonds. Preferably, the number of carbon atoms is 18–22 and the number of double bonds is 3–6. Such an oil should contain DHA, EPA or α-linolenic acid. Such a PUFA-containing oil may be at least one fish oil selected from the group consisting of skipjack oil, tuna oil, sardine oil, Alaska pollack oil, salmon oil, squid oil, mackerel pike oil, horse mackerel oil and mackerel oil, a marine animal oil such as whale oil, or a vegetable oil such as perilla oil and linseed oil, provided it contains 5% by weight or more of PUFA. Also, the oil used in the invention may be a marine animal oil, a vegetable oil, or any combination of a marine animal oil, a vegetable oil, a non-marine animal fat, and a different vegetable oil containing less than 5% by weight of PUFA.

We will discuss the diatomaceous earth used in this invention.

Generally known diatomaceous earth is fossilized siliceous shells of diatoms or aquatic single-cell phytoplanktons with their cell contents lost. Such porous diatomaceous earth is refined and used as industrial materials such as a filtering assistant, filler and building material. Large-scale deposits of such diatomaceous earth in Japan include an oceanic deposit in Akita prefecture and freshwater deposits in Oita and Okayama prefectures.

Commercially available diatomaceous earth is produced by refining raw ores of diatomaceous earth and comes in the following forms: uncalcined powder formed by pulverizing and optionally adjusting its composition and particle diameter; calcined powder formed by calcining such uncalcined powder at 900°–1200° C., powder calcined after adding 4–8% by weight of a flux such as sodium carbonate or sodium chloride (flux-calcined powder), molded articles molded into the shape of a cylinder, ring, sphere, plate or box by optionally adding forming additives such as binders; and amorphous granules obtained by crushing the molded articles.

Such diatomaceous earth originating from diatom shells has numerous pores about 100–1000 nm in diameter. Due to complicated shapes of the shells with no cell contents, the surface of such diatomaceous earth is undulated in an extremely complicated manner, creating a high porosity of about 60–90%.

The diatomaceous earth used in this invention is a powder obtained by calcining after adding 0.5–12% by weight of at least one flux selected from the group consisting of alkali metallic salts, alkali earth metallic salts, hydroxides of alkali metals and hydroxides of alkali earth metals to the above-mentioned uncalcined powder of diatomaceous earth.

The flux used in calcining the diatomaceous earth is added to the earth before calcining and used to aggregate the shells into large masses by partially melting them during sintering.

The flux used in the invention may be an alkali metallic salt such as sodium carbonate or sodium chloride, an alkali earth metallic salt such as calcium carbonate or magnesium carbonate, a hydroxide of an alkali metal or alkali earth metal such as sodium hydroxide, or a mixture thereof.

The content of flux is preferably 0.5–12% by weight, though it depends on the kind of diatomaceous earth used. Less than 0.5% by weight of flux cannot form sufficiently large aggregates of shells, making it impossible to sufficiently improve various properties of the PUFA-containing oil (such as flavor and resistance to oxidation). If more than 12% by weight, it will melt the diatomaceous earth excessively during calcining, forming oversized, difficult-to-handle aggregates.

The PUFA-containing oil is refined by bringing it into contact with powdered diatomaceous earth formed by calcining with a flux added, after subjecting the oil to alkali refining (separation of free fatty acids with alkalis) and bleaching (adsorption e.g. using activated clay or activated carbon at high temperatures).

The refining step may be carried out in a batch process or a continuous process in which a column is used.

In the batch process, the flux-calcined diatomaceous earth is added by 0.1 part by weight or more, practically 0.1–10 parts by weight, per 100 parts by weight of PUFA-containing oil. After mixing them, the mixture is filtered to batch off the oil. If the amount of diatomaceous earth added is less than 0.1 part by weight, it will be impossible to sufficiently improve the flavor of the PUFA-containing oil and its resistance to oxidation after refinement. Adding more than 10 parts by weight is meaningless because no further improvement in such properties can be expected, though no harm is done, either. Preferably, the flux-calcined diatomaceous earth should be added by 3–8 parts by weight per 100 parts by weight of PUFA-containing oil.

The PUFA-containing oil should be brought into contact with the flux-calcined diatomaceous earth at an oil temperature from 5° to 80° C. If this temperature is lower than 5° C., the PUFA-containing oil will half solidify, making the handling difficult. At temperatures higher than 80° C., it is impossible to improve the flavor and the resistance to oxidation of the refined PUFA-containing oil as expected. Rather, the effects will be lower at such high temperatures. Preferable contact temperature is 25°–45° C.

The PUFA-containing oil should be brought into contact with the flux-calcined diatomaceous earth for 10 minutes or longer to achieve the effects.

In the continuous process in which a column is used, 100 parts by weight of PUFA-containing oil is passed through the column filled with 50–100 parts by weight of flux-calcined diatomaceos earth. The contact temperature is determined on the same principle as in the batch process. The PUFA-containing oil should be retained in the column for 10 minutes or longer to achieve the object of the invention.

It is possible to further improve the oxidation resistance and the flavor of the PUFA-containing oil by deodorizing it by conventional steam distillation under vacuum after refining.

(EXAMPLES)

The types and physical properties of the diatomaceous earths used in Examples and Comparative Examples are shown in Table 1.

It was impossible to form diatomaceous earth (C) in Table 1, which contained 15% by weight of flux, into powder form.

(Example 1)

1000 grams of skipjack oil (containing 25% DHA and 6% EPA) as a PUFA-containing oil subjected to alkali refining and bleaching that are ordinarily carried out in refining food oils was put in a 2-liter beaker, and agitated for one hour at 40° C. for contact treatment after adding 50 grams of diatomaceous earth (A) in Table 1. After this contact treatment, the oil was separated from the diatomaceous earth by filtering and deodorized at 215° C. for one hour by steam distillation in which steam is blown in under a reduced pressure of 3 Torr.

The DHA content in the fatty acid in the deodorized oil was measured by gas chromatography. The DHA content was 23.5%, while the EPA content was 5.8%.

In order to determine the odor level and peroxide level of the oil after storing, 100 grams of the deodorized oil was put in a 200-milliliter ground-glass bottle after adding 3000 ppm of mixed tocopherols (made by EIZAI). After storing it for 30 hours at 60° C., it was subjected to an odor sensory test and peroxide measurement test.

In the odor sensory test, three each male and female adults were selected as panellists to evaluate the odor level in points graduated to the first decimal place by the following standards. The points shown in Table 2 are the average of the points given by the panellists. Table 2 also shows the peroxide content (meq/kg).

5.0: no fishy smells at all
4.0: slight fishy smells
3.0: moderate fishy smells
2.0: strong fishy smells
1.0: stimulative fishy smells

(Examples 2–8)

The same oil used in Example 1 was brought into contact with diatomaceous earth in exactly the same way as in Example 1, except that the diatomaceous earth (A) was replaced with diatomaceous earth (B) (Example 2), flux-calcined diatomaceous earth (D) (Example 3), flux-calcined diatomaceous earth (E) (Example 4), flux-calcined diatomaceous earth (F) (Example 5), flux-calcined diatomaceous earth (G) (Example 6), flux-calcined diatomaceous earth (H) (Example 7), and flux-calcined diatomaceous earth (I) (Example 8). Then, they were subjected to filtering, deodorization and addition of tocopherols in the same manner as in Example 1. After measuring their DHA contents, they were stored under exactly the same conditions as in Example 1 and their odor levels and peroxide levels were determined. The results are shown in Table 2.

(Comparative Examples 1–5)

The same oil used in Example 1 was brought into contact with diatomaceous earth in exactly the same way as in Example 1, except that the diatomaceous earth (A) was not used (Comparative Example 1), powdered activated carbon was used (Comparative Example 2), silica gel was used (Comparative Example 3), uncalcined diatomaceous earth (J) containing no flux was used (Comparative Example 4), and calcined diatomaceous earth (K) containing no flux was used (Comparative Example 5). They were subjected to filtering, deodorization and addition of tocopherols in the same manner as Example 1. After measuring their DHA contents, they were stored under exactly the same conditions as in Example 1 and their odor levels and peroxide levels were determined. The results are shown in Table 2.

As shown in Table 2, for Comparative Example 2, which used activated carbon, and Comparative Example 5, which used calcined diatomaceous earth (K) without a flux, the fish oil smelled fishy when it had been stored for 30 hours, though its peroxide level was low. For Comparative Example 3, which used silica gel, and Comparative Example 4, in which was used uncalcined dried diatomaceous earth (J), the fish oil smelled fishy and the peroxide level was high after 30 hours' storage.

In contrast, Examples 1–8, which were treated by bringing them into contact with diatomaceous earth calcined with a flux added, were markedly low in peroxide level compared with Comparative Examples 1–5 and achieved good results in the sensory test.

(Examples 9–11)

The same oil used in Example 1 was brought into contact with diatomaceous earth in exactly the same way as in Example 1, except that the contact treatment was carried out for one hour at 25° C. using 30 grams of diatomaceous earth (A) shown in Table 1 (Example 9), that the contact treatment was carried out for 10 minutes at 5° C. using 1 gram of diatomaceous earth (A) (Example 10), and that the contact treatment was carried out for 10 minutes at 80° C. using 1 gram of diatomaceous earth (A) (Example 11). The oils obtained were then filtered and deodorized, and their DHA contents were measured in the same way as in Example 1. After measuring their DHA contents, they were stored under exactly the same conditions as in Example 1 and their odor levels and peroxide levels were determined. The results are shown in Table 3.

(Comparative Examples 6)

The same oil used in Example 1 was brought into contact with diatomaceous earth, filtered and deodorized in exactly the same way as in Example 1, except that the contact treatment was carried out for one hour at 100° C. using diatomaceous earth (A) shown in Table 1. The oils thus obtained were stored under exactly the same conditions as in Example 1 and their odor levels and peroxide levels were determined. The results are shown in Table 3.

As shown in Table 3, Examples 9–11, which satisfy all the treatment conditions with diatomaceous earth, were low in peroxide level and had little fishy smells after storage. But when the oil was treated at 100° C. by bringing it into contact with diatomaceous earth, the oil produced fishy smells though its peroxide level was kept low, in spite of the fact that the diatomaceous earth used had been treated with a flux added.

(Example 12)

30 grams of diatomaceous earth (A) shown in Table 1 was filled into a column 105 $cm^2$ in volume, and the column was placed in a constant temperature bath kept at a constant temperature of 40° C. Skipjack oil pretreated (alkali refined and bleached) under the same conditions as in Example 1 was passed through the column at a rate of 1 milliliter/minute for an hour.

The oil obtained was stored under the same conditions as in Example 1 and its peroxide level and odors were measured. The results are shown in Table 4.

As shown in Table 4, when 100 parts by weight of diatomaceous earth was brought into contact with 100 parts by weight of PUFA-containing oil, the peroxide level and fishy smells after storage were the lowest.

(Example 13)

A mixture of 750 grams of skipjack oil and 250 grams of corn oil (DHA 16.7%, EPA 3.5%) as a PUFA-containing oil was treated in exactly the same way as in Example 9. The oil thus obtained was stored under the same conditions as in Example 9 and its peroxide level and odors were measured. The results are shown in Table 5.

(Comparative Example 7)

The same oil used in Example 13 was treated in exactly the same manner as in Example 13 except that it was not treated with diatomaceous earth calcined with a flux added. The oil obtained was stored under the same conditions as in Example 13 and its peroxide level and odors were measured. The results are shown in Table 5.

As shown in Table 5, it is impossible to suppress the peroxide level and fishy smells of a PUFA-containing oil simply by adding corn oil thereto. But by treating such a mixture of oils with diatomaceous earth (A) calcined with a flux, its peroxide level and fishy smells after storage decreased markedly.

(Example 14)

500 grams of alkali refined and bleached perilla oil (containing 19.5% oleic acid, 15.9% linoleic acid and 59.2% α-linolenic acid) as a PUFA-containing oil was put in a 1-liter beaker, together with 25 grams of diatomaceous earth (A) shown in Table 1, and agitated for one hour at 40° C. for contact treatment. After the treatment, the diatomaceous earth was separated by filtering. The oil thus obtained was deodorized by steam distillation for one hour at 215° C. under a reduced pressure of 3 Torr.

The PUFA content in the fatty acid in the deodorized oil was measured by gas chromatography. The content of α-linolenic acid was 57.9%.

This oil was stored under the same conditions as in Example 1, and 48 hours later, its peroxide level and odor level were measured. The results are shown in Table 6. In the odor sensory test, the odor level was evaluated in the following four stages, because unlike fish oils, this oil has no strong smells.

◎ no peculiar smells at all
○ no smells
Δ slight smells
X intense smells (Comparative Example 8)

The same oil used in Example 14 were treated in exactly the same way as in Example 14 except that no diatomaceous earth was used. The oil obtained were stored under the same conditions as in Example 14 and its peroxide level and odor level were measured. The results are shown in Table 6.

As shown in Table 6, it is possible to suppress the peroxide level and odor levels of even perilla oil, a PUFA-containing vegetable oil by treating it with diatomaceous earth calcined with a flux added.

According to this invention, an oil containing polyunsaturated fatty acids is refined by bringing it into contact with diatomaceous earth calcined with a flux added. The refining and manufacturing method can suppress fishy or other peculiar odors which are produced due to oxidation of PUFA and conversion of odor-emanating precursors into odor-emanating substances when the fat and oil is added to a food or while a food containing such a fat and oil is stored.

TABLE 1

| Type of diatomaceous earth | | Item: Type of flux used | Content of flux in wt % | Average particle size in μm | Condition of diatomaceous earth |
|---|---|---|---|---|---|
| Flux-calcined diatomaceous earth | (A) | Sodium carbonate | 7 | 33 | White powder |
| Flux-calcined diatomaceous earth | (B) | Sodium carbonate | 0.5 | 18 | Pink powder |
| Flux-calcined diatomaceous earth | (C) | Sodium carbonate | 15 | — | Not obtained |
| Flux-calcined diatomaceous earth | (D) | Sodium carbonate | 7 | 500 | White granule |
| Flux-calcined diatomaceous earth | (E) | Sodium carbonate 50% Sodium chloride 50% | 6 | 33 | White powder |
| Flux-calcined diatomaceous earth | (F) | Potassium chloride | 6 | 33 | White powder |
| Flux-calcined diatomaceous earth | (G) | Calcium carbonate | 6 | 33 | Salmon-pink powder |
| Flux-calcined diatomaceous earth | (H) | Magnesium carbonate | 6 | 33 | Salmon-pink powder |
| Flux-calcined diatomaceous earth | (I) | Sodium hydroxide | 5 | 33 | White powder |
| Dried diatomaceous earth | (J) | — | — | 11 | Light brown powder |
| Calcined diatomaceous earth | (K) | — | — | 13 | Salmon-pink powder |

TABLE 2

| No. | Item: Sensory evaluation point | Peroxide number in meq/kg |
|---|---|---|
| Example 1 | 4.1 | 2.70 |
| Example 2 | 3.9 | 3.45 |
| Example 3 | 4.2 | 2.50 |
| Example 4 | 4.0 | 2.89 |
| Example 5 | 3.9 | 3.11 |
| Example 6 | 4.0 | 3.05 |
| Example 7 | 3.8 | 2.96 |
| Example 8 | 3.8 | 4.09 |
| Comparative example 1 | 2.5 | 9.22 |
| Comparative example 2 | 2.5 | 5.91 |
| Comparative example 3 | 2.5 | 5.30 |
| Comparative example 4 | 3.3 | 5.81 |
| Comparative example 5 | 3.5 | 5.15 |

TABLE 3

| No. | Item: Sensory evaluation point | Peroxide number in meq/kg |
|---|---|---|
| Example 9 | 4.0 | 2.34 |
| Example 10 | 3.8 | 3.85 |
| Example 11 | 3.8 | 4.17 |
| Comparative example 6 | 3.3 | 4.77 |

TABLE 4

| No. | Item: Sensory evaluation point | Peroxide number in meq/kg |
|---|---|---|
| Example 12 | 4.2 | 2.47 |

TABLE 5

| No. | Item: Sensory evaluation point | Peroxide number in meq/kg |
|---|---|---|
| Example 13 | 4.2 | 1.89 |
| Comparative example 7 | 2.8 | 8.26 |

TABLE 6

| No. | Item: Sensory evaluation point | Peroxide number in meq/kg |
|---|---|---|
| Example 14 | ⊙ | 1.43 |
| Comparative example 8 | Δ | 1.69 |

What is claimed is:

1. A method of refining at least one member selected from the group consisting of a fat and an oil containing polyunsaturated fatty acids having 18 or more carbon atoms and three or more double bonds, said method comprising the step of bringing 100 parts by weight of said at least one member into contact for 10 minutes or more at 5°–80° C. with not less than 0.1 part by weight of powdered or granulated diatomaceous earth formed by calcining with a flux added.

2. A method as claimed in claim 1 wherein said flux is selected from the group consisting of alkali metallic salts, alkali earth metallic salts, hydroxides of alkali metals and hydroxides of alkali earth metals and is added in an amount of 0.5–12% by weight to said powdered or granulated diatomaceous earth.

3. A method as claimed in claim 1 or 2 wherein said at least one member to be refined contains 5% by weight or more of polyunsaturated fatty acids and is a marine animal oil, a vegetable oil, or any combination of a marine animal oil, a vegetable oil, a non-marine animal fat, and a different vegetable oil containing less than 5% by weight of polyunsaturated fatty acid.

* * * * *